(12) United States Patent
Lee

(10) Patent No.: US 12,171,449 B2
(45) Date of Patent: Dec. 24, 2024

(54) THROMBECTOMY AND STENTING SYSTEM

(71) Applicant: Neuravi Limited, Galway (IE)

(72) Inventor: Declan Lee, Longford (IE)

(73) Assignee: Neuravi Limited, Galway (IE)

( * ) Notice: Subject to any disclaimer, the term of this patent is extended or adjusted under 35 U.S.C. 154(b) by 0 days.

(21) Appl. No.: 18/534,875

(22) Filed: Dec. 11, 2023

(65) Prior Publication Data
US 2024/0108370 A1 Apr. 4, 2024

Related U.S. Application Data

(62) Division of application No. 16/670,440, filed on Oct. 31, 2019, now abandoned.

(51) Int. Cl.
| | | |
|---|---|---|
| *A61B 17/221* | (2006.01) | |
| *A61B 17/22* | (2006.01) | |
| *A61B 17/3207* | (2006.01) | |
| *A61F 2/90* | (2013.01) | |
| *A61F 2/958* | (2013.01) | |
| *A61F 2/962* | (2013.01) | |

(52) U.S. Cl.
CPC ........ *A61B 17/221* (2013.01); *A61B 17/3207* (2013.01); *A61F 2/90* (2013.01); *A61F 2/958* (2013.01); *A61F 2/962* (2013.01); *A61B 2017/22079* (2013.01); *A61B 2017/2215* (2013.01)

(58) Field of Classification Search
CPC .............. A61B 17/221; A61B 17/3207; A61B 2017/22079; A61B 2017/2215; A61B 2017/22034; A61F 2/90; A61F 2/962; A61F 2/958
See application file for complete search history.

(56) References Cited

U.S. PATENT DOCUMENTS

| | | |
|---|---|---|
| 6,391,037 B1 | 5/2002 | Greenhalgh |
| 6,540,722 B1 | 4/2003 | Boyle et al. |
| | (Continued) | |

FOREIGN PATENT DOCUMENTS

| | | |
|---|---|---|
| WO | 2014/008460 A1 | 1/2014 |
| WO | 2017/040681 A1 | 3/2017 |

OTHER PUBLICATIONS

Extended European Search Report issued in corresponding European Patent Application No. 20 20 4898 dated Mar. 30, 2021, 8 pages.

*Primary Examiner* — Kelly J Bekker
*Assistant Examiner* — Andrew P. Restaino
(74) *Attorney, Agent, or Firm* — Troutman Pepper Hamilton Sanders LLP

(57) ABSTRACT

A design capable of both mechanical thrombectomy and stenting for treating occlusions in the cerebral vasculature provides for a three-catheter setup. The first outer catheter has the largest diameter and can serve as a guide catheter while also being a sheath for the other catheters. The second deployment catheter can be configured for the aspiration of occlusions and can include a stepped or recessed section proximal of the distal tip that can act as a housing for a braided expandable stent. The outer diameter of this stepped section can be lined with an inflation device on top of which the braided stent sits. Internal to the second deployment catheter is a microcatheter which can deliver mechanical thrombectomy devices to the target site to retrieve an occlusion in the vessel, after which the stent can be expanded and implanted in the vessel.

17 Claims, 8 Drawing Sheets

(56) References Cited

U.S. PATENT DOCUMENTS

| | | |
|---|---|---|
| 8,858,497 B2 | 10/2014 | Di Palma et al. |
| 9,157,174 B2 | 10/2015 | Kusleika |
| 9,232,992 B2 | 1/2016 | Heidner |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 2002/0095141 A1 | 7/2002 | Belef et al. |
| 2004/0215229 A1 | 10/2004 | Coyle |
| 2005/0113862 A1 | 5/2005 | Besselink et al. |
| 2005/0288695 A1 | 12/2005 | Jenson et al. |
| 2006/0064151 A1 | 3/2006 | Guterman |
| 2008/0269868 A1 | 10/2008 | Bei et al. |
| 2008/0281350 A1 | 11/2008 | Sepetka |
| 2010/0004650 A1 | 1/2010 | Ormsby et al. |
| 2010/0004674 A1 | 1/2010 | Stalker |
| 2010/0211094 A1 | 8/2010 | Sargent, Jr. |
| 2010/0324649 A1 | 12/2010 | Mattsson |
| 2011/0034937 A1 | 2/2011 | Mustapha et al. |
| 2012/0283768 A1 | 11/2012 | Cox et al. |
| 2014/0018842 A1 | 1/2014 | Cully et al. |
| 2014/0135812 A1 | 5/2014 | Divino et al. |
| 2014/0200607 A1 | 7/2014 | Sepetka et al. |
| 2015/0238207 A1 | 8/2015 | Cox et al. |
| 2016/0317185 A1 | 11/2016 | Krieger et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2019/0216476 A1 | 7/2019 | Barry et al. |

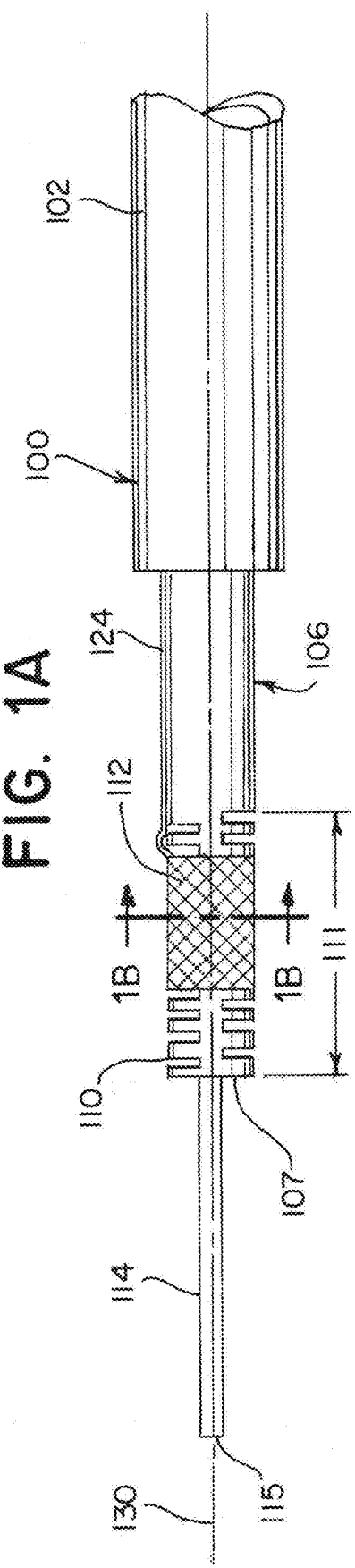
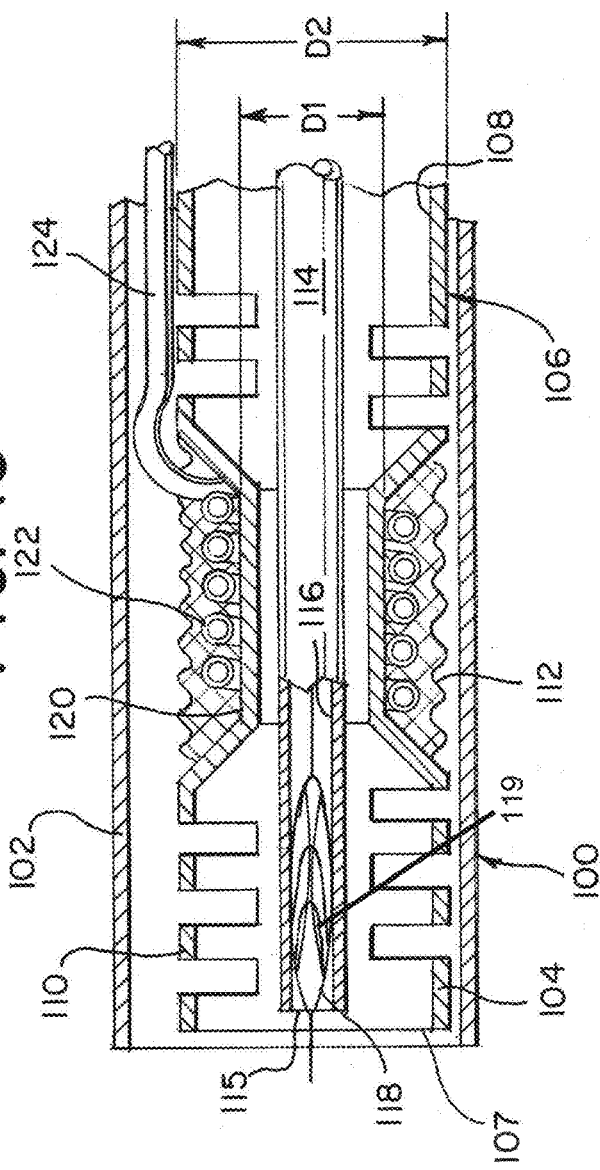
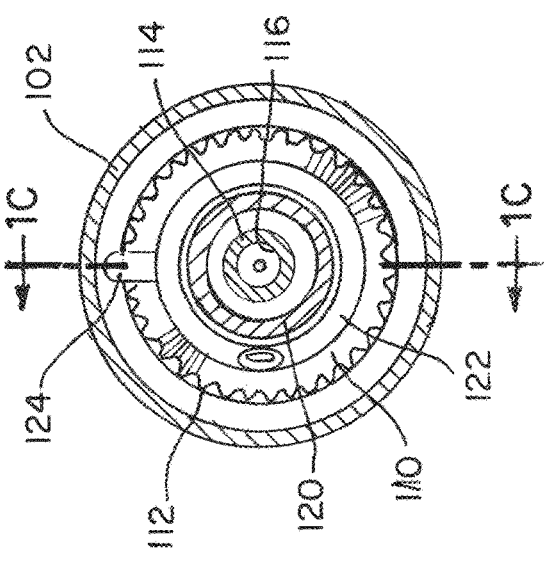

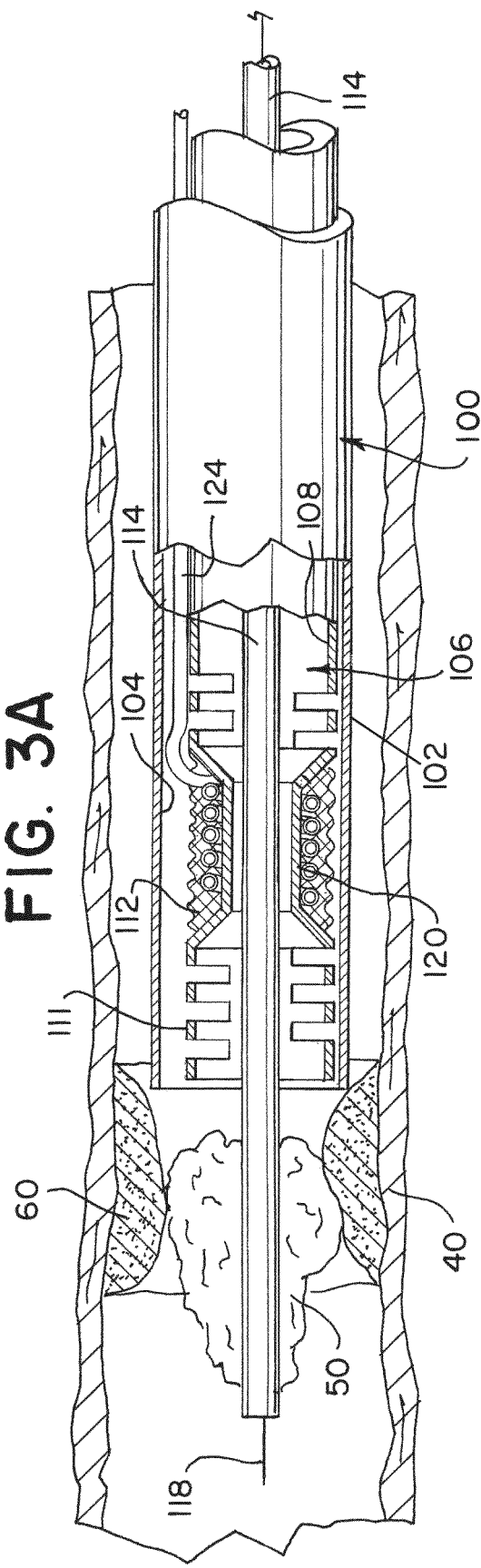
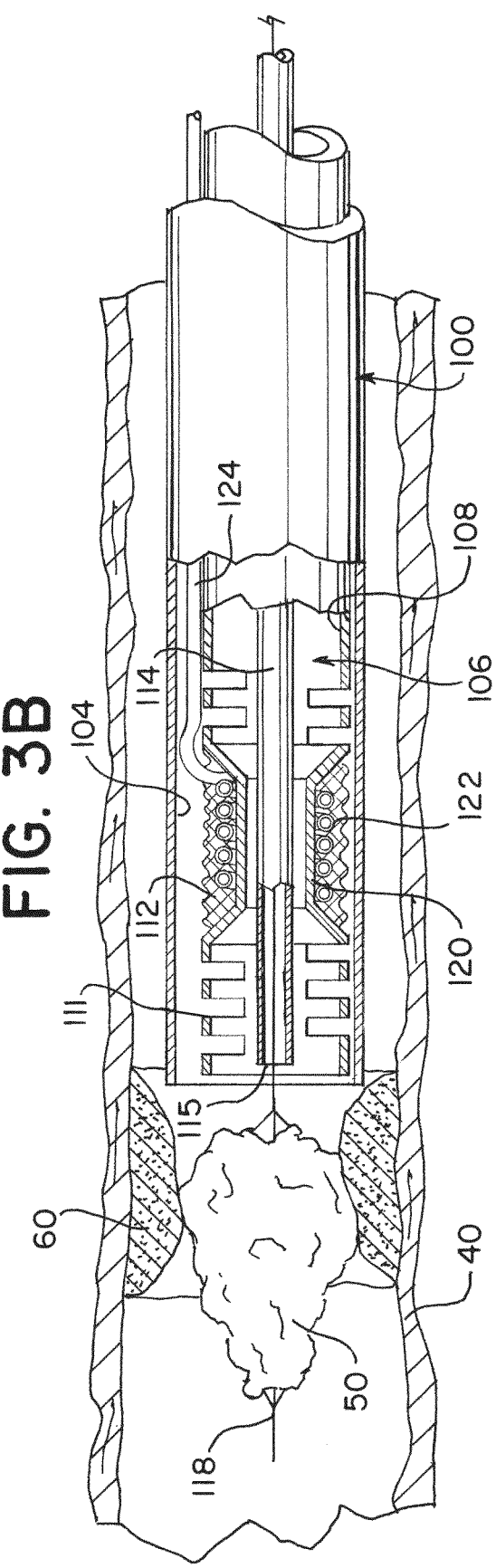

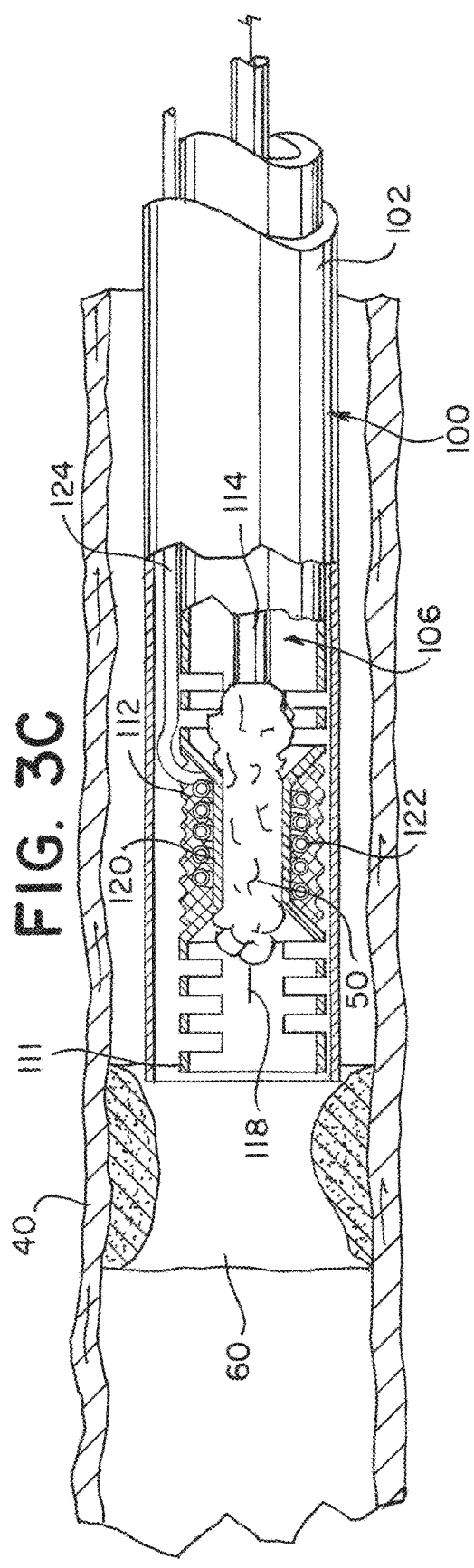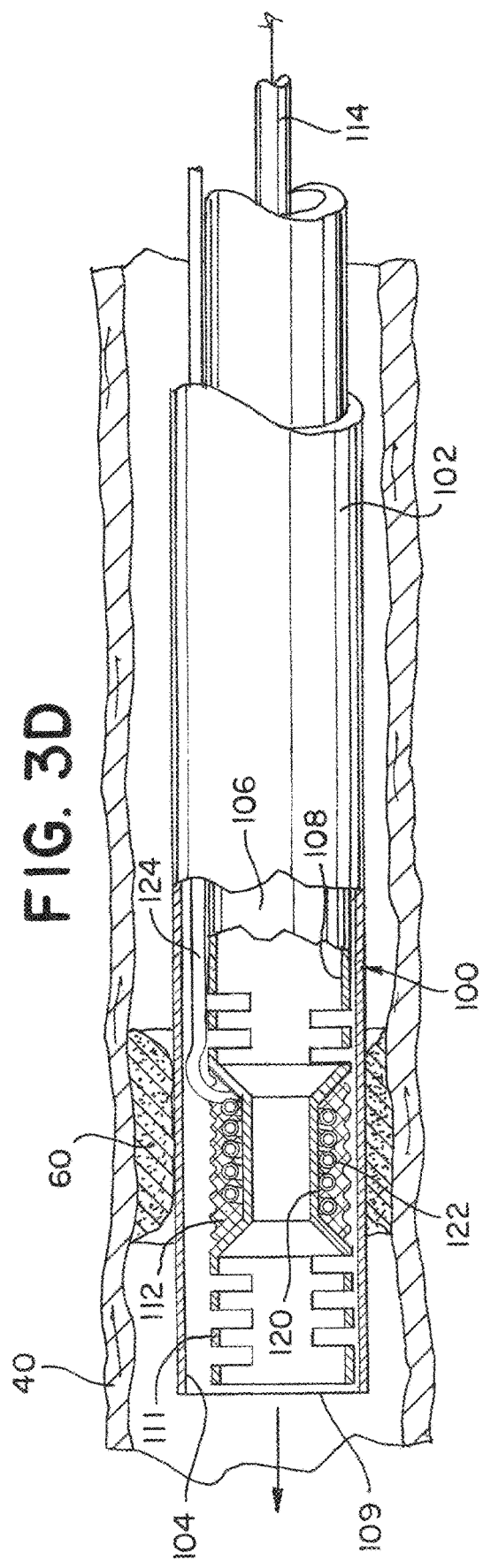

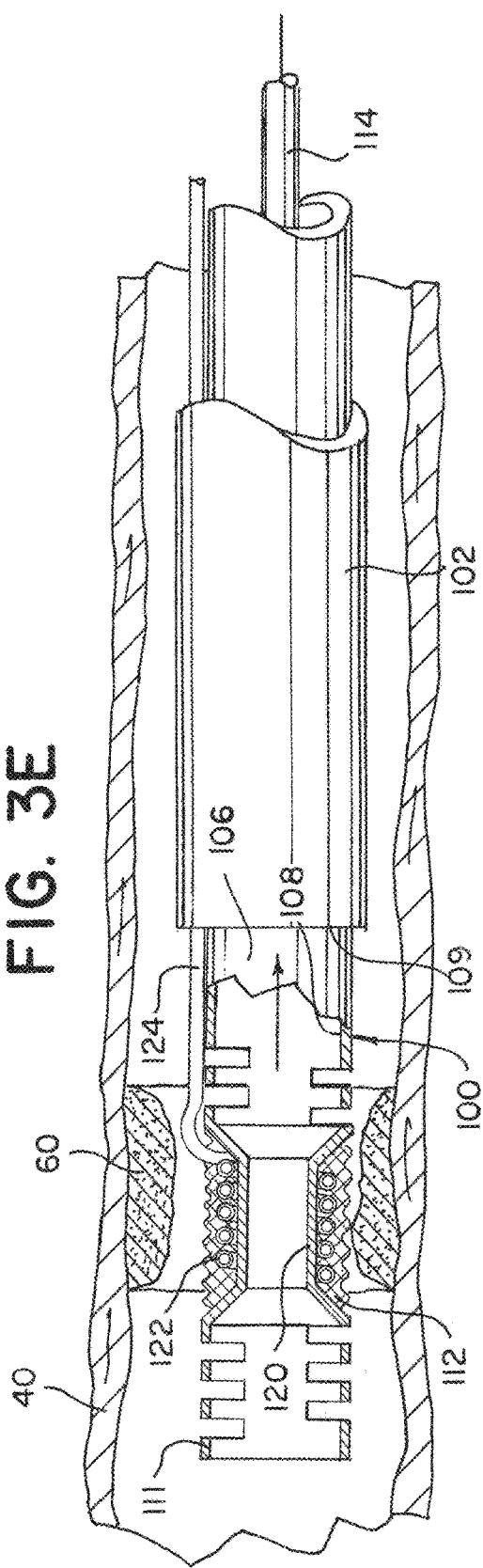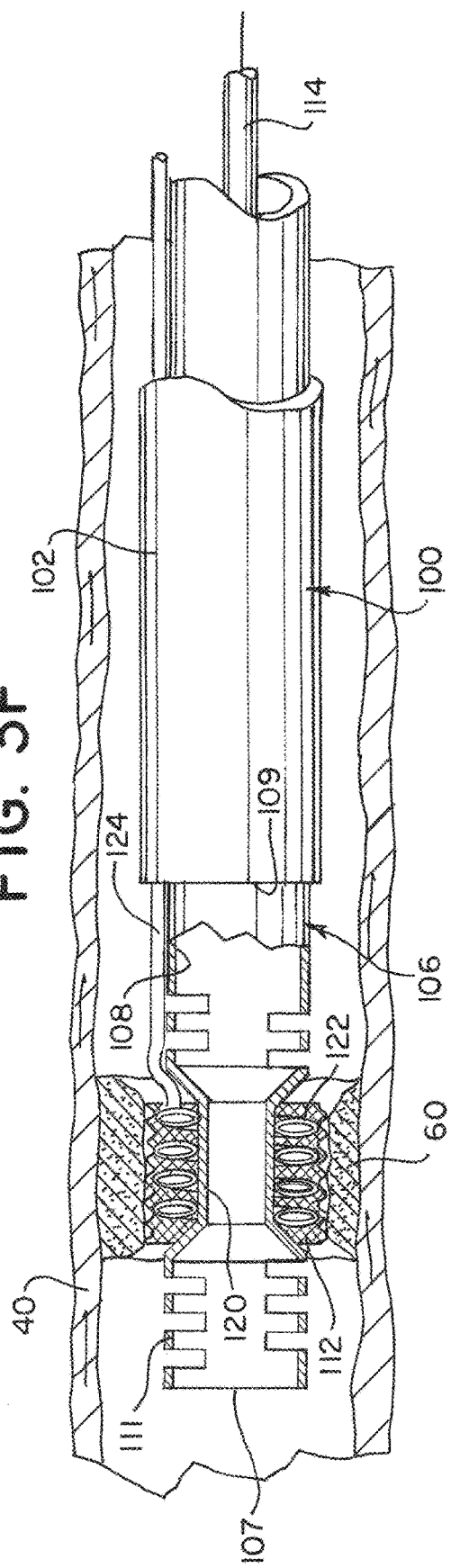

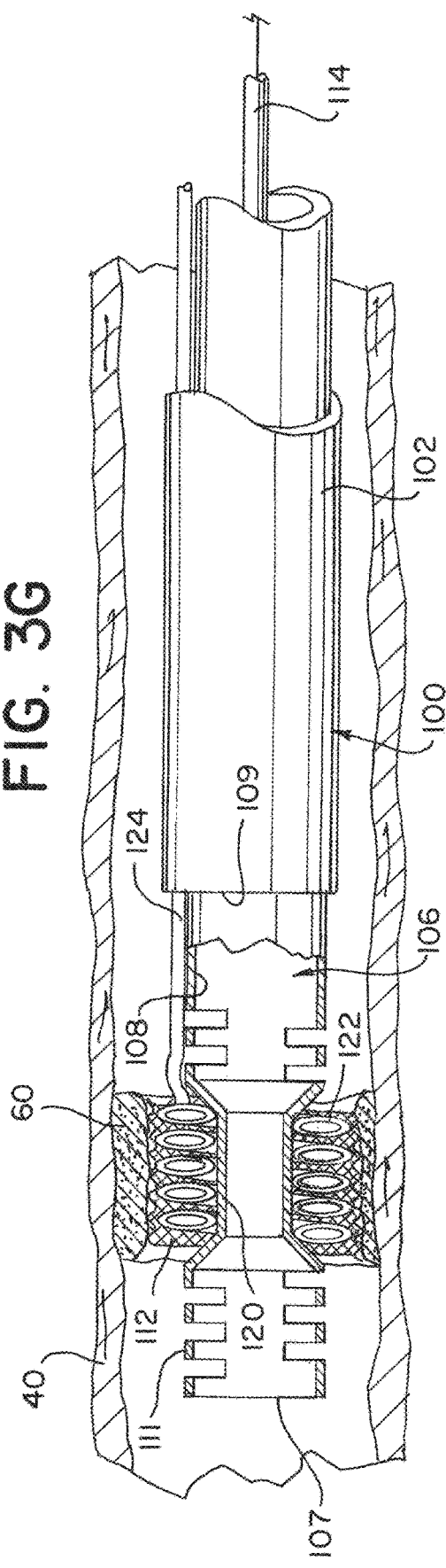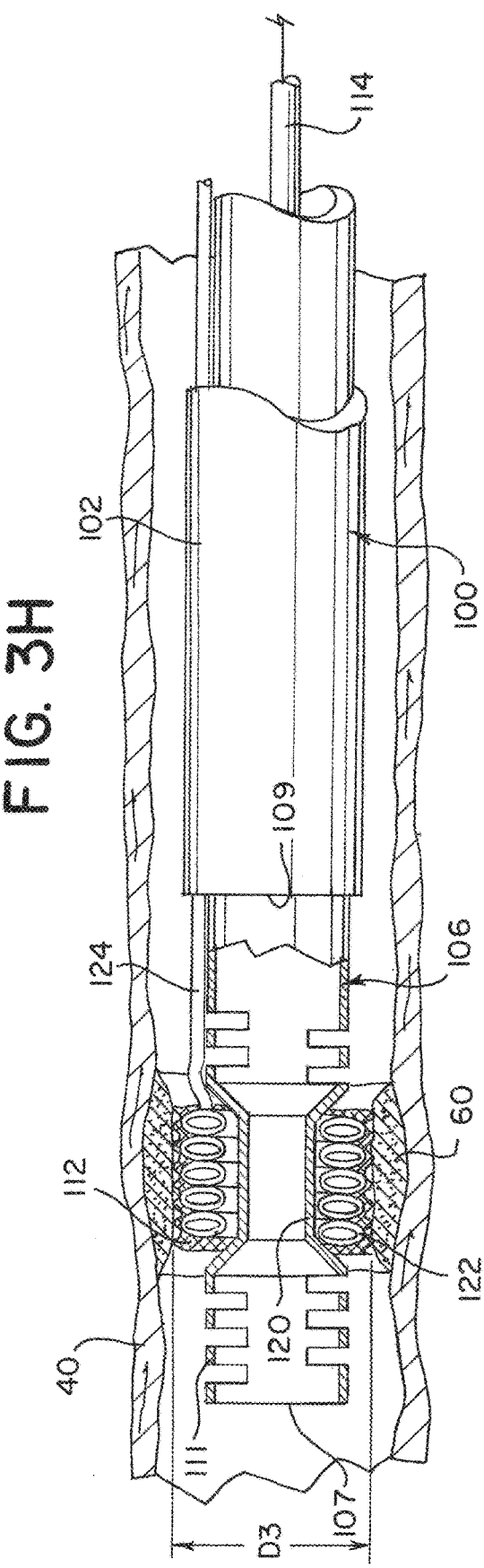

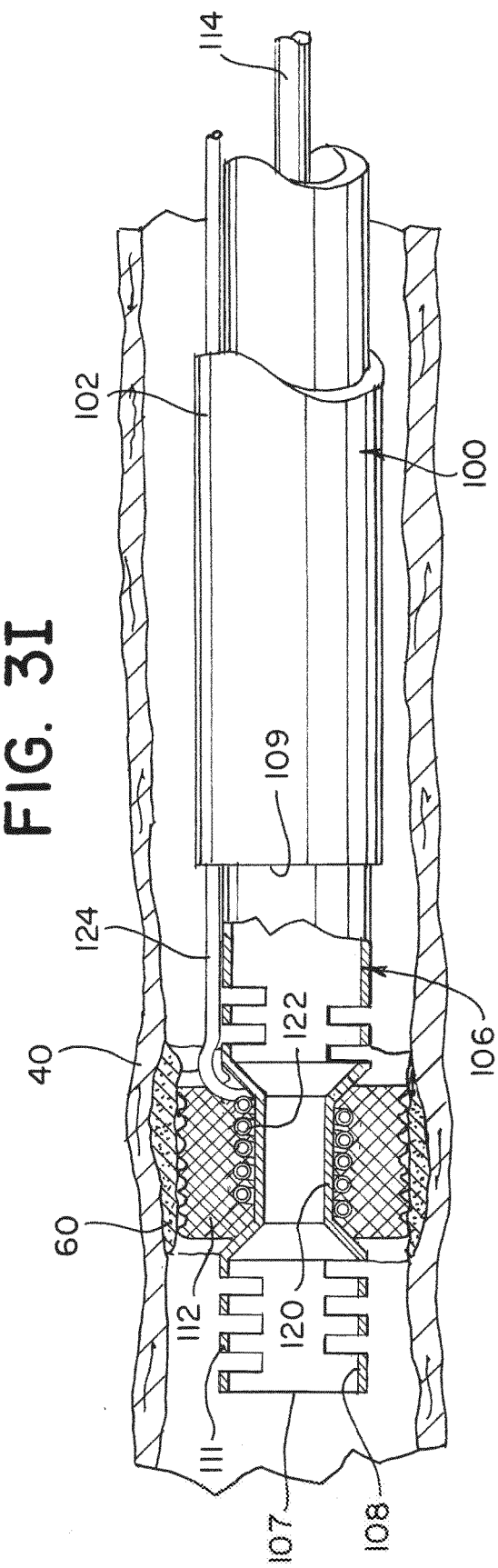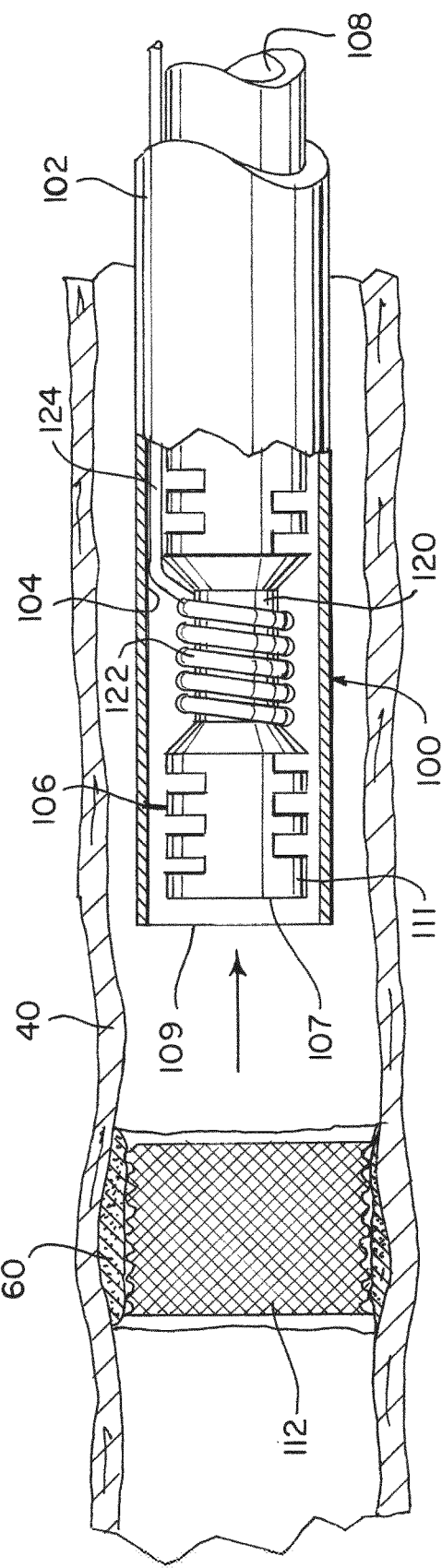

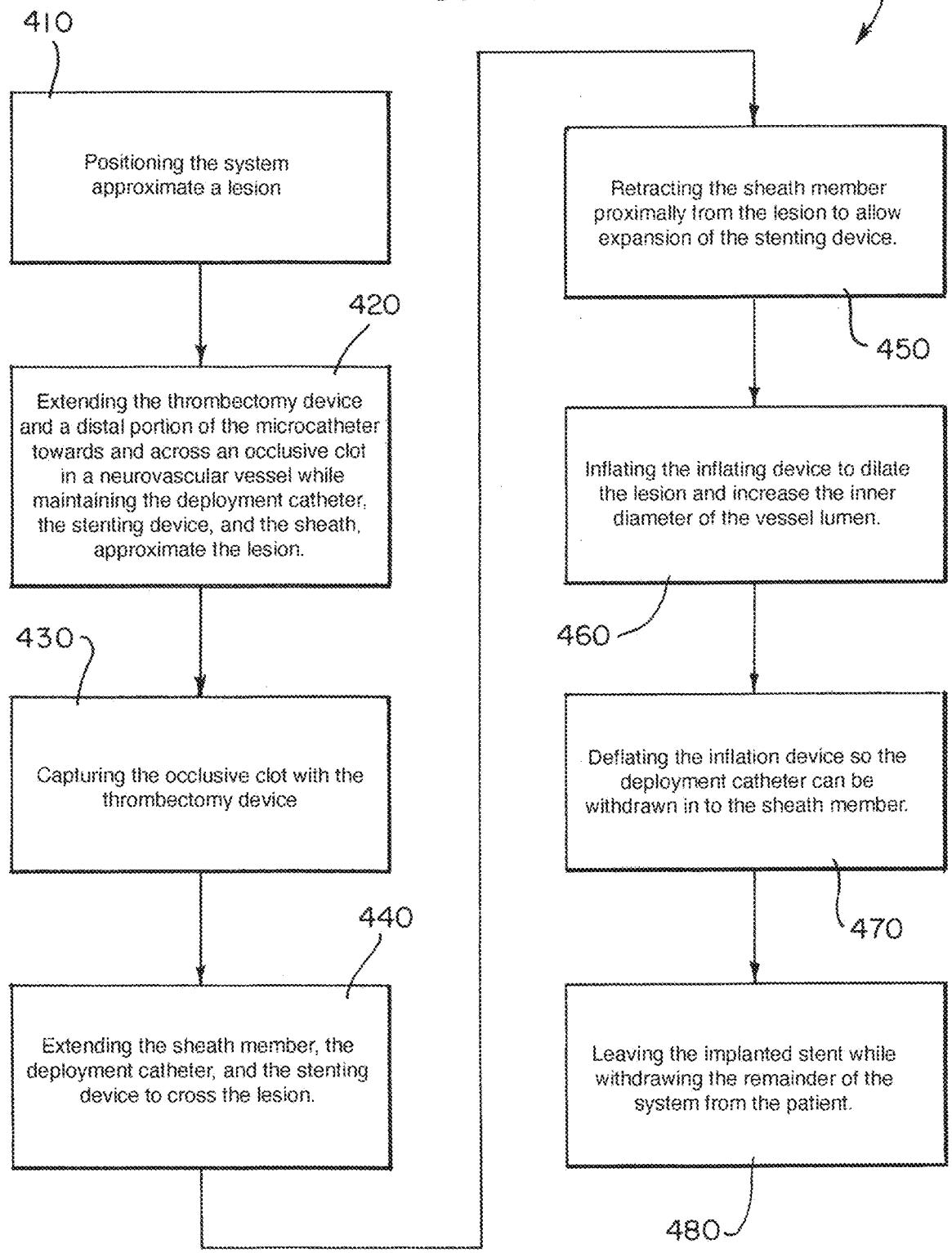

THROMBECTOMY AND STENTING SYSTEM

CROSS REFERENCE TO RELATED APPLICATION

The present application is a divisional application of U.S. patent application Ser. No. 16/670,440 filed Oct. 31, 2019. The entire contents of which are hereby incorporated by reference.

FIELD OF THE INVENTION

The present invention generally relates devices and methods used in removing obstructions and treating stenosis in the cerebral blood vessels during intravascular medical treatments. More specifically, the present invention relates to a multi-catheter system for bringing together the procedures of mechanical thrombectomy and stenting.

BACKGROUND

Atherosclerosis results from lesions which narrow and reduce the space in the lumen of vessels in the vasculature. Such lesions are usually composed of plaque, which can be fat, cholesterol, calcium, or other components of the blood. Severe occlusion or closure can impede the flow of oxygenated blood to different organs and parts of the body and result in other cardiovascular disorders such as heart attack or stroke. Narrowing of vessels, or stenosis, increases the risk that clots and other emboli can lodge at such locations, especially in the neurovascular bed where vessel diameters are already small. Intracranial atherosclerotic disease (ICAD) is the narrowing of those arteries and vessels supplying blood to the brain and represents the most common proximate mechanism of ischemic stroke.

Treatment for vascular occlusions are well known in the art. Methods can include utilizing drugs, such as anticoagulants or anti-platelet agents, as well as medical procedures such as surgical endarterectomy, angioplasty, and stenting. Much of the recent success in endovascular revascularization treatments (ERT) has been the further development of safe thrombectomy devices. Devices such as stentrievers, direct-aspiration systems, and other clot retrieval devices have been strongly associated with better clinical outcomes. However, these devices are primarily designed to recanalize the vessel by removing and retrieving an occluding embolus. Sufficient recanalization may not occur if there is also significant stenosis present at the occlusion site, increasing the need for implanted stents.

Treatment methods for addressing clots and lesions in the neurovascular bed in particular depend on the degree of stenosis, the shape of the target occlusion site (i.e. truncal, branching, etc.), and the patient's overall condition. Mechanical procedures often involve using medical devices to retrieve an occlusive clot and then utilizing balloons and stents to open a narrowed artery. Following the use of a stentriever or other clot retrieval device, a balloon is delivered to a target site and inflated to dilate the stenosis. The balloon can then be removed and exchanged through a catheter for a stent delivery device. If desirable, once the stent is in place a balloon can be inflated inside the stent to press the struts of the stent frame firmly against the inner wall of the vessel.

However, various significant challenges exist in interpreting and diagnosing the stenosis in the first place. This is especially in the very small and tortuous vessels of the cerebral vasculature. During the treatment of stroke or transient ischemic attack, it can be unknown if the occlusion is the result of a blood clot alone of if a stenosis is also present. Identifying stenotic lesions can be arduous because it is difficult to differentiate them from clots and other embolism-related occlusions through baseline angiography. In many cases the presence of the stenosis is only identified after initial treatment options are chosen and an ERT procedure is already underway, and the devices and methods used to remove occlusions are often different from those used to treat stenosis and stent a vessel.

In cases where both a blood clot and stenosis are present, the physician can often be required to change out catheters, devices, and often guidewires after removing the clot. Devices offering procedural flexibility are thus highly valuable, as the need for multiple passes and device deliveries can be cumbersome and these mechanical treatments further create the potential of releasing additional fragments into the vasculature. Such fragments can include but are not limited to blood clots, plaque, and other thrombi debris.

The need for shorter door-to-procedure times in is always present to limit lasting damage in ischemic stroke patients. Therefore, there remains a need for new systems and devices to continue to address and improve these treatments. The present design is aimed at providing an improved system and method for treating the combined presence of clots and stenosis in the cerebral vasculature which addresses the above-stated deficiencies.

SUMMARY

It is an object of the present design to provide systems, devices, and methods to meet the above-stated needs. Generally, the proposed system provides for a three-catheter setup. The first catheter has the largest diameter and can serve as a guide catheter while also being a deployment sheath for the other catheters. The second catheter can be configured for aspiration and can include a stepped or recessed section proximal of the distal tip that can serve as a housing for a braided expandable stent. The outer diameter of this stepped section can be lined with a balloon or other inflatable member on top of which the flexible stent sits. Internal to the second catheter is a microcatheter which can deliver mechanical thrombectomy devices to the target site to retrieve an occlusion in the vessel.

An example system for removing a clot from and stenting a blood vessel can include a sheath member, a deployment catheter, and a microcatheter. The three catheters can be substantially concentric. A source can be configured to aspirate the internal lumen of the sheath member and/or deployment catheter. The deployment catheter can have a lumen and an outer surface and be disposed within the lumen of the sheath member. The deployment catheter can have a flexible distal portion and a recessed region on its outer surface with an outer diameter less than the outer diameter of the deployment catheter in a region adjacent to the recessed region. The flexible region can enhance deliverability and encompass the distalmost region of the deployment catheter. For example, the flexible region could extend 15-30 centimeters proximal of the distal tip.

An inflation device and a stenting device can circumscribe the recessed region of the deployment catheter outer surface. The recessed region can provide a seat for the inflation and stenting devices on the outer surface and provide for a more low-profile system. The stenting device could be self-expandable, or the inflation device can be used to expand the stenting device in a stenotic lesion and implant it as a stent, similar to traditional methods for balloon angioplasty known in the art. Inflation could be accomplished by utilizing an inflation lumen which could run the length of the deployment catheter. The inflation device could also be used to dilate the vessel during any part of the stenting procedure.

For retrieval of obstructions in vessels, the system can be used as an aspiration catheter utilizing suction to remove an occlusive clot. In situations where a clot has become lodged in a vessel or a region of constricted stenosis, the system can retrieve the clot by aspirating the clot into the lumen of the deployment catheter, or by utilizing other mechanical thrombectomy procedures. For example, the third catheter of the system can be a microcatheter situated in the lumen of the deployment catheter and configured to deliver a mechanical thrombectomy device to a target occlusion. The mechanical thrombectomy device can be any of a number of commercially-available designs. In one example, an expandable clot retriever which has a collapsed configuration inside the microcatheter but self-expands into an enlarged deployed configuration upon exiting the lumen at the distal tip. The clot engaging portion of the device can have expandable members which can create a flow lumen across an occlusion when deployed, while also having a plurality of struts which imbed to provide a strong grip on the clot for the initial step of disengaging the clot from the vessel. To then remove the clot, the device could be retracted proximally into the deployment catheter with aspiration. The device and clot can then either be withdrawn from the patient through the lumen of the catheter or can be drawn back far enough to lodge a firmer clot in the tip of a larger catheter to be withdrawn in tandem with the catheter.

In another example, a thrombectomy and stenting system for removing a clot from a blood vessel and stenting the blood vessel can include a sheath member, a deployment catheter situated in the lumen of the sheath member, and a microcatheter situated in the lumen of the deployment catheter. The sheath member, deployment catheter, and microcatheter can be concentric with one another and configured to move independently along a longitudinal axis of the system. An expandable stenting device can be coupled to an outer surface of the deployment catheter. The microcatheter can contain a clot retrieval device for capturing and removing the clot from the vessel.

The body of the stenting device can have a braided or interlinking pattern with a matrix of sufficient density to support the walls of the vessel when implanted. The mesh tube of the stent can be of medical-grade stainless steel, such as 316 SS, or a cobalt or cobalt-chrome alloy. In other examples, the stent can be of polymeric or partial-polymeric construction. The mesh braid could also be made from a shape-memory allow such that it self-expands upon deployment. The stent can be bare metal, or the material can be coated with a non-pharmacological coating such as silicon carbide, carbon, and titanium-nitride-oxide. In other cases, stents have been coated with biodegradable, drug-eluting coatings designed to inhibit restenosis. These coatings could be anti-platelet or anti-coagulative agents to help prevent clot formation after the procedure.

In one example, a portion of the deployment catheter outer surface can contain a depressed region having a dimension that is less than a dimension of another region of the deployment catheter adjacent to the depressed region. The depressed region can be formed integrally with the body of the deployment catheter, such as a notch or groove cut into the outer surface of the deployment catheter. For example, if the supporting structure for the deployment catheter is formed from a hypotube, the depressed region could be laser cut into the outer surface. Further features could also be cut into the surface to improve flexibility and trackability of the catheter. The expandable stenting member can be sized so that the member is situated on or housed in the depressed region. In some cases, the system can also have an inflation device which is circumscribed with the stenting device on the outer surface of the deployment catheter. When the user wishes to implant a stent in a region of stenosis, the sheath member can be withdrawn to expose the stenting device. The inflation device can then be inflated to expand the stenting device scaffolding and exert a radial force on the walls of the vessel.

Also provided is a method for using a system offering the flexibility of both mechanical thrombectomy and stenting procedures. The method can have some or all of the following steps and variations thereof, and the steps are recited in no particular order. A patient's vasculature is accessed using conventionally-known techniques. A sheath member is positioned approximate a stenotic lesion and occlusive clot. A deployment catheter is disposed within the lumen of the sheath member. A microcatheter containing a thrombectomy device is positioned in the lumen of the deployment catheter. A stenting device comprising an inflation device and a stent is positioned on an outer surface of the deployment catheter approximate the distal end of the catheter. An aspiration source, such as a vacuum pump or syringe, is configured to direct aspiration through the lumen flow path of one or both of the sheath member and deployment catheter. Aspiration can be utilized both for clot retrieval and for preventing additional embolization.

The microcatheter and thrombectomy device are extended towards and across the occlusive lot while maintaining the sheath, deployment catheter, and the stenting device approximate the lesion. The clot can be aspirated through the lumen of the deployment catheter. The clot is captured by deploying the thrombectomy device from the microcatheter by maintaining the position of the thrombectomy device across the clot and retracting the microcatheter proximally. The microcatheter and thrombectomy device with the captured clot can then be withdrawn into the lumen of the deployment catheter. Alternatively, the sheath member, deployment catheter, and stenting device can be advanced over the thrombectomy device to cross and align with the stenosis. Once in position, the sheath member can be retracted proximal of the lesion to expose the stenting device.

The inflation device of the stenting device can be inflated, radially expanding both the inflation device and stent across the lesion. This radial expansion can increase the diameter of a first portion of the vasculature comprising the lesion to at least 75% of the diameter of a second portion of the vasculature adjacent to the first portion. This process opens the vessel and reduces the narrowing/occlusion caused by the stenosis. Once the desired expansion is achieved, the stent can be released in place as an implant by deflating the inflation device. Once the stent is in place, the remainder of the system can be withdrawn from the patient.

Having the flexibility to conduct mechanical thrombectomy and stenting operations with a single system, such as the current design, can greatly reduce procedure times and thus result in better clinical outcomes. This is particularly true in the case of stroke patients.

Other aspects and features of the present disclosure will become apparent to those of ordinary skill in the art, upon reviewing the following detailed description in conjunction with the accompanying figures.

BRIEF DESCRIPTION OF THE DRAWINGS

The above and further aspects of this invention are further discussed with the following description of the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation. It is expected that those of skill in the art can conceive of and combining elements from multiple figures to better suit the needs of the user.

FIGS. 1A-1C are views of the three-catheter system according to aspects of the present invention;

FIGS. 3A-3J show cross sections which illustrate the steps of using the system to perform a mechanical thrombectomy and stenting procedure according to aspects of the present invention;

FIG. 3A illustrates the system at the target site and the microcatheter advanced across the occlusive clot according to aspects of the present invention;

FIG. 3B illustrates the thrombectomy device of the system deployed to capture an occlusive clot according to aspects of the present invention;

FIG. 3C shows the thrombectomy device and captured clot being withdrawn back inside the system according to aspects of the present invention;

FIG. 3D shows the remainder of the system being advanced to a position where the stenting device is aligned with the lesion according to aspects of the present invention;

FIG. 3E illustrates the outer sheath member being retracted to expose the stenting device according to aspects of the present invention;

FIG. 3F shows the inflation of the inflation device radially expanding the stenting device to widen the narrowed vessel according to aspects of the present invention;

FIG. 3G shows the continued inflation of the inflation device to widen the vessel according to aspects of the present invention;

FIG. 3H shows the full desired inflation of the inflation device and the stent embedded in the vessel according to aspects of the present invention;

FIG. 3I shows the deflation of the inflation device to release the stent in place according to aspects of the present invention;

FIG. 3J shows the withdrawal of the remainder of the system leaving the stent implanted according to aspects of the present invention;

FIG. 4 is a flow diagram outlining a method for using the system to conduct mechanical thrombectomy and stenting operations according to aspects of the present invention.

DETAILED DESCRIPTION

Figure 2:
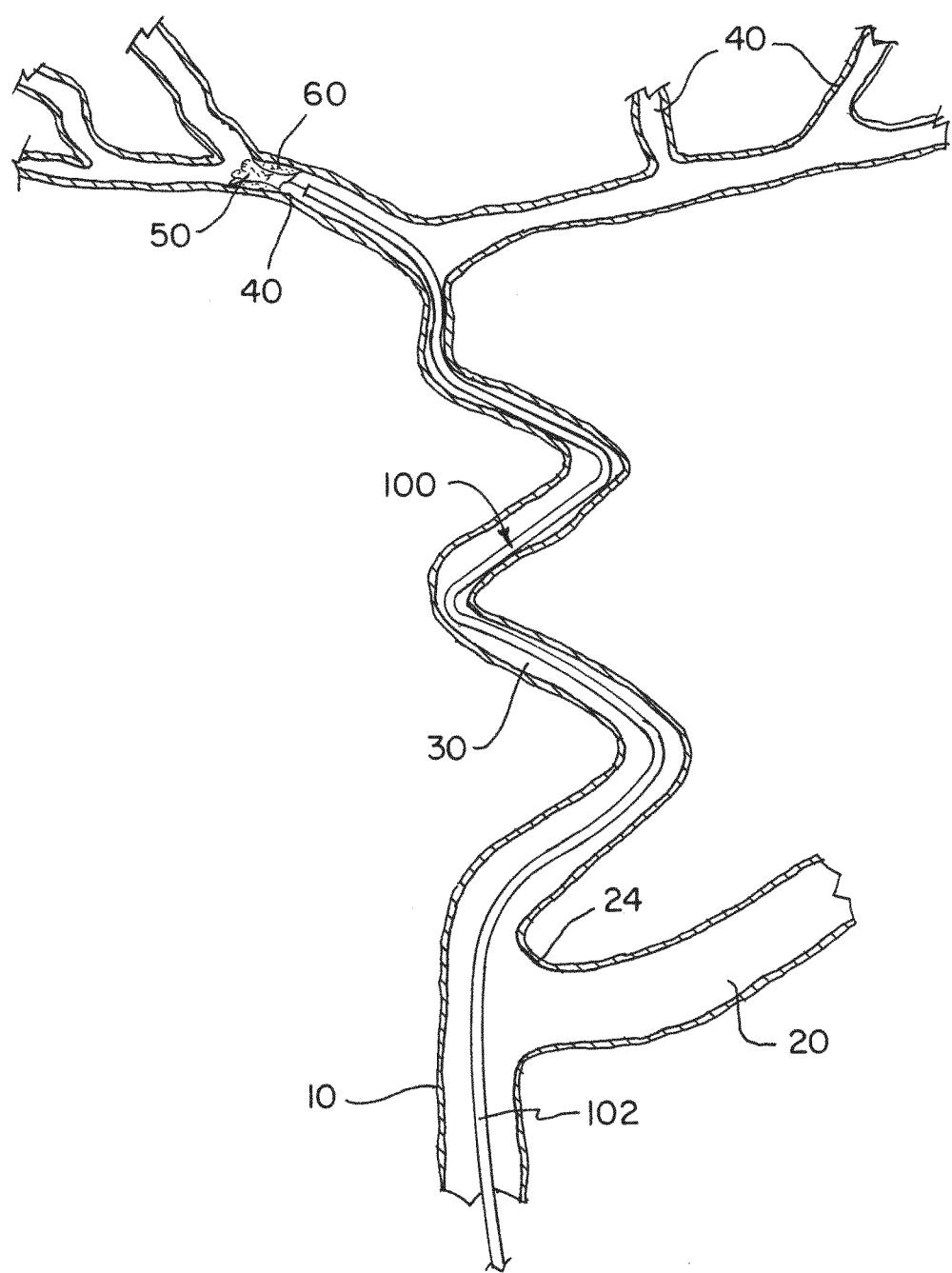
FIG. 2 shows the system at a target location in the neurovascular vessel with a stenotic lesion and an occlusive clot according to aspects of the present invention.

Specific examples of the present invention are now described in detail with reference to the Figures, where identical reference numbers indicate elements which are functionally similar or identical. It is an object of the current invention to offer a system or device which gives the physician the advantage of operational flexibility to adapt to complications or unknowns in an intravascular procedure, such as when an occluded vessel has a blood clot and also a region of underlying stenosis which was not detected during angiography. These improvements can lead to safe and more rapid access to complex areas of the intercranial arteries to remove occlusions and shorten procedure times.

Accessing the various vessels within the vasculature, whether they are coronary, pulmonary, or cerebral, involves well-known procedural steps and typically the use of a number of conventional, commercially-available accessory products. These products, such as angiographic materials, rotating hemostasis valves, and guidewires are widely used in laboratory and medical procedures. When these products are employed in conjunction with the system and methods of this invention in the description below, their function and exact constitution are not described in detail. While the description is in many cases in the context of treating intercranial arteries, the systems and devices may be used in other body passageways as well.

Turning to the figures, FIGS. 1A-1C illustrate a system 100 capable of treating both occlusions and stenosis in a blood vessel. As illustrated, the system 100 can have a first outer guide catheter or sheath member 102 having an internal lumen 104. A second deployment catheter 106 can be disposed in the lumen 104 of the sheath member 102. The sheath member 102 can act as a guide catheter for the system 100. The sheath member can also serve as a deployment sleeve for the deployment catheter, protecting the rest of the system during delivery and deployment.

As illustrated in the cross-sectional view in FIG. 1C, the deployment catheter 106 can have a distal end 107, an outer diameter D2, an outer surface 110, an inner lumen 108, and a flexible portion 111 disposed circumferentially in an annular pattern around the outer surface approximate the distal end. The deployment catheter can also have a stepped or depressed region 120 just proximal of the distal end 107 of the catheter where the depressed region outer diameter D1 is less than the nominal deployment catheter outer diameter D2. The depressed region 120 thus can represent a recess or groove-like feature of the deployment catheter. The depressed region can take on a trapezoidal shape with shallow corners or could assume a number of other shapes, such as a half ellipse, so long as it is at least partially recessed from the outer surface of the deployment catheter 106 and rings at least a portion of the circumference.

An expandable stenting device 112 can be disposed concentrically to circumscribe the outer circumference of an uninflated inflation device 122 and approximate to the flexible portion 111 of the deployment catheter 106. The stenting device can be disposed within the flexible portion of the deployment catheter. In one example, the flexible portion 111 extends proximally from the distal end 107 of the deployment catheter 106 for a length of approximately 20 cm.

Both the stenting device and the inflation device can circumscribe the deployment catheter. In one example, the expandable stenting device 112 can be a stent having a plurality of resilient metal or plastic strands formed in a braided pattern. The stenting device can be self-expanding when deployed from the system or could be expanded with the aid of the inflation device 122. In one example, this braid of the implantable stent of the stenting device can be of any of a number of stainless-steel alloys, or of a cobalt or cobalt-chrome alloy construction. In other examples, the stent braid can be made of polymeric strands.

In still other cases the braid of the stenting device 112 can be manufactured from Nitinol or a similar superelastic alloy having the shape-memory properties of a tubular structure with a predetermined outer diameter. A self-expanding stenting device could be actuated by retracting the outer sheath member 102 and might not require a separate inflation device 122 for deployment, but a balloon could still be used for pre- or post-dilation of the vessel during the implantation process. This tubular structure can be heat treated on a mandrel to a suitable temperature to anneal the structure, causing the tube to conform to the shape of the mandrel. In these ways the elastic properties of the stent braid could be controlled such that the stent can self-expand to aid in the implantation process. The properties are also important so the stent can maintain stiffness and strength over the desired lifetime of the implant. The winding of the braid strands can also be sufficiently dense to provide a stable configuration capable of supporting the full inner circumference of a vessel when implanted.

In another example, the strands or struts of the stent can extend longitudinally and be woven in a largely helical configuration with the central axis or centerline 130 of the resulting tubular structure as a common axis. A first set of strands can be wound in one direction while being axially displaced from one another. A second group of strands could be wound in the opposite direction from the first while also being axially displaced relative to each other.

The stenting device can also be bare metal or could be coated in a number of ways. The coating can be hydrophilic or have additives effective to increase the lubricity of the mesh braid of the stenting device 112 to allow for more atraumatic navigation of the vasculature. In another example, the coating could be hydrogel or include soluble particles in a polymeric matrix which could soften or fully dissolve when exposed to an aqueous medium like blood. In a further example, the coating could have embedded pharmaceutical agents, such as anti-platelet, anti-coagulant, anti-inflammatory, or anti-microbial agents. These agents could elute from the matrix of the coating when exposed to aqueous media and help prevent the implanted stent from forming a potential nidus for future clot formation.

The inflation device 122 can be coupled, glued, or welded to the outer surface 110 of the deployment catheter. The inflation device 122 can have one or more balloon or innertube-type members of varied construction and an expanded condition configured to expand and implant the stenting device 112. Inflation of the inflation device can be accomplished through an inflation lumen or tube 124 running the length of the deployment catheter 106. The inflation tube can occasionally be an independent member, but more often can be a hollow lumen incorporated into the internal construction of the deployment catheter. The expandable stenting device and inflation device can together circumscribe the depressed region 120 of the deployment catheter 106 and together the assembly could have a nominal radial dimension similar to the nominal outer diameter D2 of the deployment catheter. The depressed region 120 within the flexible distal section 111 of the deployment catheter 106 can be a housing for the inflation device 122 and stenting device 112 during delivery of the system 100. The longitudinal length of depressed region 120 could be such that the region could accommodate the most common neurovascular stent sizes.

The balloon can be constructed of any of a number of materials, such as Chronoprene, Polyurethane, Nylon, PBx, or another thermoplastic elastomer. These materials allow the balloon to be durable and thin. The final shape of the balloon or balloons could be varied and tailored to the shape of the stenting device 112. In one instance, the balloon could have a substantially tubular profile with conical ends.

It should be noted that when an element is described and visualized in the figures as a tubular structure and generally illustrated as a substantially right cylindrical structure, when used herein, the terms "tubular" and "tube" are to be construed broadly. They are not meant to be limited to a structure that is a right cylinder or strictly circumferential in cross-section or of a uniform cross-section throughout its length.

Also illustrated in FIG. 1C is a microcatheter 114 which can be disposed within the lumen 108 of the deployment catheter 106. The microcatheter can be concentric with both the guide/sheath member 102 and deployment catheter 106 about the central longitudinal axis 130 of the system 100. The sheath member, deployment catheter, and microcatheter can be independently moveable with respect to one another. The deployment catheter can be used to first aspirate an occlusive clot 50, after which if necessary, the microcatheter can be used for the delivery and deployment of a mechanical thrombectomy device 118. The mechanical thrombectomy device can be any of a number of commercially available products. The device can have a clot retriever with a clot engaging portion having a collapsed delivery configuration within the microcatheter and be self-expanding to an expanded deployed configuration once emerged from the distal tip 115 of the microcatheter. The engaging portion can have an expandable network of struts 119 for gripping the clot and dislodging it from the vessel. The shape of the network can be designed such that when the device 118 is retracted, the struts 119 exert a force on the clot in a direction substantially parallel to the direction in which the clot 50 is being pulled from the vessel (i.e. substantially parallel to the longitudinal axis 130 of the system). This limits the outward radial force applied to the vessel, meaning the action of the thrombectomy device does not serve to increase the force needed to actually dislodge the clot from the vessel. This atraumatic function is important for the often-fragile vessels of the neurovascular bed 40.

It is of benefit to have the microcatheter 114 and thrombectomy device 118 deploy and retract from within the lumen 108 of the deployment catheter 106 so the clot retrieval process can be kept isolated from and not interfere with the stenting process. Similarly, a thrombus could be aspirated and retrieved through the inner lumen of the deployment catheter without the use of the thrombectomy device.

In some situations, the physician may wish to reverse the flow of blood in the target vessel. Reversing flow prevents any emboli from migrating downstream in the vasculature. Aspiration can be directed through the lumen 104 of the sheath member 102, deployment catheter 106, or both. To isolate any one catheter lumen of the system for aspiration, a seal could be formed between the inner and outer surfaces of the catheters. For example, if the aspiration source was connected to the lumen 104 at the proximal end of the guide sheath 102, suction could be directed to the mouth at the distal end 107 of the deployment catheter 106 by utilizing a seal of hydrogel between the outer surface 110 of the deployment catheter and the inner wall of the sheath member. In another example, an expandable member or frame could be used as a flow restriction between the surfaces. The low-pressure region could thereby be transferred to the distal end 107 of the deployment catheter 106. In some cases, it may be possible to aspirate a clot or debris directly into the lumen 108 of the deployment catheter without the need to use the microcatheter 114 and thrombectomy device 118.

In another example, a thrombectomy and stenting system 100 for removing a clot from and stenting a neurovascular blood vessel 40 can include a sheath member 102, a deployment catheter 106 disposed in a lumen 104 of the sheath member, a microcatheter 114 oriented in a lumen 108 of the deployment catheter, and a thrombectomy device 118 arranged in a lumen 116 of the microcatheter. The sheath member 102, deployment catheter 106, and microcatheter 114 can be substantially concentric and configured to move independently of each other along a longitudinal axis A1. Aspiration for supported procedures can be directed to the mouth at the distal end 107 of the deployment catheter. The thrombectomy device can have an expandable framework of struts or crowns configured to grip and remove an occlusive clot 50.

The outer surface 110 of the deployment catheter 106 can also have a depressed region 120. The depressed region can have a first radial dimension D1 less than a second radial dimension D2 of another region of the outer surface adjacent to the depressed region. The deployment catheter 106 can have an expandable stenting device 112 coupled to the deployment catheter outer surface 110. The stenting device can circumscribe the depressed region 120, such that it is substantially radially flush with the outer surface 110. An inflation device 122 configured to expand the stenting device 112 can also be included and coupled to the outer surface of the deployment catheter. In one example, the inflation device is a circumferential balloon that could be inflated by a contrast liquid media. At least a portion of the stenting device 112 can circumscribe the inflation device 122.

FIG. 2 shows the composite system 100 navigated through the internal Carotid artery 30 to a target site within the neurovascular vessel 40. The target site can be a vessel occluded as shown, with an obstructive clot lodged in an area of intercranial stenosis in the form of a lesion 60 caused by the buildup of atherosclerotic plaque. An advantage offered by the system as seen in FIG. 2 is that the guide catheter or sheath member 102 of the system can act as a sleeve capable of protecting internal components of the system during navigation to the site. Other designs for balloon-expandable coronary stents can run the risk of shearing the stent off of the balloon prior to arriving at the target lesion due to the tortuosity and varied diameters of the cerebral vasculature. This is part of the reason that considerable effort has been devoted to the development of low-profile balloon catheters. The recessed or stepped section 120 as described herein can allow for a more compact system 100 to be employed since it enables an outer sheath member 102 of a smaller diameter to be used while still shielding the system.

FIGS. 3A-3J show cross sections which illustrate example steps of one way of using a system of the invention to perform a mechanical thrombectomy and subsequent stenting procedure. When the system 100 is advanced to a location just proximal to the target lesion 60 and occlusive clot 50, the deployment catheter 106 can be used as an aspiration catheter to aspirate the occlusion into the lumen 108 of the deployment catheter for removal. For stickier, more obstinate obstructions, the microcatheter 114 can be advanced beyond the distal end 107 of the deployment catheter 106 and across the clot until the distal end 115 is distal of the clot, as shown in FIG. 3A. A guidewire could also be used for positioning the microcatheter. In many cases, radiopaque markers or coils can also be added to various portions of the device and/or catheter to aid the user in determining when the device is appropriately positioned across the clot. For example, a coil of radiopaque material, such as tungsten and/or platinum, can be attached to the distal end of the thrombectomy device so that the terminal end can be visualized readily during the treatment procedure. Once in the proper position, the thrombectomy device 118 can be unsheathed as the microcatheter 114 is withdrawn proximally, allowing the thrombectomy device to expand within and to either side of the clot 50, as shown in FIG. 3B. The scaffold of the capture portion of the device expands to grip portions of the clot.

Once the user is satisfied the thrombectomy device 118 has a firm grip on the clot 50, the device can be withdrawn proximally back into the deployment catheter 106, as shown in FIG. 3C. This could be done with the aid of aspiration through the deployment catheter 106 to help sustain a firm grip on the clot and avoid fragment loss and migration. If desired, the user can completely remove the thrombectomy device and microcatheter from the system 100 and patient to allow for more efficient aspiration during subsequent steps. Multiple passes with the microcatheter and thrombectomy device may also be necessary to sufficiently clear the vessel.

After the occlusive clot has been safely secured and withdrawn, the remainder of the system 100 within the sheath member 102 can be advanced across the stenosis, such that the stenting device 112 and inflation device 122 are aligned with the lesion 60, as seen in FIG. 3D. Good alignment can ensure that the radial force exerted on the vessel when they stenting device is expanded is distributed as uniformly as possible along the longitudinal length of the device. As with the thrombectomy procedure from FIG. 3B, proper alignment can be achieved with the placement of radiopaque markers or coatings. Once aligned across the lesion, the sheath member 102 can be retracted so that the sheath distal end 109 returns proximal to the stenosis to expose the stenting device 112, as seen in FIG. 3E.

Once exposed, the stenting device 112 can self-expand or be radially expanded by the inflation device 122. The inflatable members of the inflation device 122 can be filled with a working fluid, typically a contrast medium, via the inflation lumen or tube 124. Once inflation commences, the inflation device can radially expand the stenting device 112 as illustrated in FIG. 3F. As the inner diameter of the target vessel is constricted by stenosis, the outer surface of the stenting device can first contact the plaque or fatty deposits of the lesion 60. FIG. 3G shows that as the outer diameter of the stenting device continues to grow, this contact can gently exert a compressive radial force on the lesion by squeezing it between the stenting device and vessel wall. Once the lesion can no longer be further compressed, continued inflation can dilate and enlarge the luminal diameter until a desired implant diameter D3 of the vessel is reached, as demonstrated in FIG. 3H. In one example, this desired diameter is reached when a constricted first diameter in the portion of the vessel containing the lesion increases to 75% of a second diameter in a portion of the vessel adjacent to the first.

In an alternate step, the stenting device 112 can be a self-expanding structure configured to assume a predetermined outer diameter when deployed without the need for an inflation device 122. The outer diameter for the device can be chosen such that a desired radial force is applied to the vessel and an implant diameter D3 sufficient to recanalize flow.

After the expansion has reopened the occluded neurovascular vessel 40, the stenting device 112 can be left in place as an implanted stent by deflating the inflation device 122. This could be accomplished by attaching an aspiration source to the proximal end of the inflation tube 126. Aspiration could continue until the inflation device had shrunk to a diameter approximate the diameter D2 of the outer surface 110 of the deployment catheter 106. Alternatively, aspiration could continue until the inflation device had shrunk to a diameter less than the inside diameter of the sheath member 102, allowing the deployment catheter to be retracted into the lumen 104 of the sheath member 102, as shown in FIG. 3I and FIG. 3J. No longer pinned by the inflation device, the expanded stenting device 112 remains in place as a stent to ensure the patency of the target vessel lumen.

FIG. 4 is a flow diagram including method steps for administering an intravascular treatment involving thrombectomy and stenting using a system such as the examples described herein. Referring to method 400 outlined in FIG. 4, in step 410 access to a patient's vasculature is gained through traditionally known techniques and a three-catheter system is positioned approximate a lesion and occlusive clot in an occluded vessel in the neurovascular system. The first catheter can be a guide catheter or sheath member as described herein or as would otherwise be known to a person of ordinary skill in the art. The second catheter can be a delivery catheter with an inflation device and a stenting device as described herein. The delivery catheter can further be configured as an aspiration catheter. The third catheter can be a microcatheter with a lumen and a thrombectomy device therein as described herein or as would otherwise be known to a person of ordinary skill in the art.

In step 420, a distal portion of the microcatheter and the thrombectomy device is advanced from the deployment catheter towards and across an occlusive clot in a neurovascular vessel while maintaining the deployment catheter, inflation device, stenting device, and sheath approximate the lesion. In step 430, the thrombectomy device is deployed to capture the occlusive clot as illustrated and described herein or by other means, such as direct aspiration, as would be understood by a person of ordinary skill in the art. Step 430 can also include the step of retracting the captured clot, thrombectomy device, and microcatheter proximally back into the lumen of the deployment catheter. The captured clot, thrombectomy device, and microcatheter can be completely removed from the system and patient if desired by the user at this stage.

In step 440, the sheath member, deployment catheter, inflation device, and stenting device are advanced distally across the lesion. The stenting device can be aligned with the lesion. In step 450, the sheath member is retracted proximal to the lesion to expose and allow for expansion of the stenting device.

In step 460, the inflation device is inflated to expand the stenting device to dilate the lesion and increase the diameter of the vessel lumen. The stenting device can be expanded until a desired stent implant diameter is reached. In step 470, the inflation device is deflated to release pressure on the implanted stenting device and allow the deployment catheter to be withdrawn into the sheath member. In step 480, the stent is left in the vessel as an implant. Step 480 can further have the step of removing the rest of the system from the patient.

The invention is not necessarily limited to the examples described, which can be varied in construction and detail. The terms "distal" and "proximal" are used throughout the preceding description and are meant to refer to a positions and directions relative to a treating physician. As such, "distal" or distally" refer to a position distant to or a direction away from the physician. Similarly, "proximal" or "proximally" refer to a position near to or a direction towards the physician. Furthermore, the singular forms "a," "an," and "the" include plural referents unless the context clearly dictates otherwise.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology has been resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Some steps of a method can be performed in a different order than those described herein without departing from the scope of the disclosed technology. Similarly, it is also to be understood that the mention of one or more components in a device or system does not preclude the presence of additional components or intervening components between those components expressly identified. For clarity and conciseness, not all possible combinations have been listed.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%.

The descriptions contained herein are examples of embodiments of the invention and are not intended in any way to limit the scope of the invention. While particular examples of the present invention are described, various modifications to devices and methods can be made without departing from the scope and spirit of the invention. For example, while the examples described herein refer to particular components, the invention includes other examples utilizing various combinations of components to achieve a described functionality, utilizing alternative materials to achieve a described functionality, combining components from the various examples, combining components from the various example with known components, etc. The invention contemplates substitutions of component parts illustrated herein with other well-known and commercially-available products. To those having ordinary skill in the art to which this invention relates, these modifications are often apparent and are intended to be within the scope of the claims which follow.

The invention claimed is:

1. A method of using a thrombectomy and stenting system comprising: a sheath member, a deployment catheter, a stenting device comprising an inflation device and a stent, a microcatheter, and a thrombectomy device, the method comprising:
   positioning the system approximate a lesion;
   extending the thrombectomy device and a distal portion of the microcatheter towards an occlusive clot in a vasculature region while maintaining the deployment catheter, the stenting device, and the sheath member approximate the lesion;

deploying the thrombectomy device from the microcatheter;

capturing the occlusive clot with the thrombectomy device by expanding a plurality of struts of the thrombectomy device within and to either side of the occlusive clot to embed in the occlusive clot;

extending the sheath member, the deployment catheter, and the stenting device to cross the lesion such that the thrombectomy device is retracted within the deployment catheter before the stent is deployed approximate the lesion;

retracting the sheath member from the lesion;

inflating the inflation device of the stenting device across the lesion; and releasing the stent of the stenting device to cross the lesion.

2. The method of claim 1 further comprising retracting the occlusive clot into the deployment catheter.

3. The method of claim 1 further comprising positioning the deployment catheter within a lumen of the sheath member.

4. The method of claim 1 further comprising positioning the microcatheter within the deployment catheter.

5. The method of claim 1 further comprising positioning the thrombectomy device within the microcatheter.

6. The method of claim 1, wherein the stenting device comprises the stent disposed on an outer surface of the deployment catheter.

7. The method of claim 1, wherein inflating the stenting device comprises increasing a diameter of a first portion of the vasculature region comprising the lesion to at least 75% of a diameter of a second portion of the vasculature region adjacent to the first portion.

8. The method of claim 1 further comprising releasing the stent of the stenting device in proximity to the lesion by deflating the inflation device.

9. The method of claim 1 further comprising:
crossing the occlusive clot with the microcatheter and the thrombectomy device; and
retracting the microcatheter while maintaining the thrombectomy device across the occlusive clot.

10. The method of claim 1, wherein the deployment catheter is oriented within a lumen of the sheath member, the deployment catheter comprising:
a deployment catheter lumen;
a deployment catheter outer diameter;
a deployment catheter inner diameter;
a deployment catheter outer surface; and
a depressed region on the deployment catheter outer surface, and proximate to a distal end of the deployment catheter, the depressed region comprising a depressed region outer diameter configured to be less than the deployment catheter outer diameter, and a depressed region inner diameter configured to be less than the deployment catheter inner diameter and the depressed region outer diameter.

11. The method of claim 10, wherein the stenting device comprises the stent circumscribing the depressed region of the deployment catheter, and
wherein the stenting device is located at the distal end of the deployment catheter and circumscribes the deployment catheter outer surface.

12. The method of claim 10, wherein the distal end of the deployment catheter comprises a flexible portion proximal of and distal of the stenting device.

13. The method of claim 1, wherein the struts of the thrombectomy device are configured to deploy from a lumen of the microcatheter and retract within a lumen of the deployment catheter.

14. The method of claim 1, wherein the inflation device is coupled to an outer surface of the deployment catheter, wherein a portion of the stenting device circumscribes the inflation device, and wherein the inflation device has an expanded condition configured to expand the stenting device.

15. The method of claim 1, wherein a lumen of the sheath member, a lumen of the deployment catheter and a lumen of the microcatheter are substantially concentric.

16. The method of claim 1, wherein the thrombectomy device comprises an expandable clot retriever collapsible to fit within a lumen of the microcatheter and self-expandable upon exiting the microcatheter lumen, the expandable clot retriever comprising a capture portion expandable to grip portions of the occlusive clot.

17. The method of claim 1, wherein the thrombectomy device and the microcatheter are withdrawn from the deployment catheter before the sheath member is advanced across the lesion and the sheath member is retracted such that a distal end of the sheath member is located proximal of the lesion to expose the stent.

* * * * *